United States Patent
García-revillo García et al.

(10) Patent No.: US 10,702,218 B2
(45) Date of Patent: Jul. 7, 2020

(54) PROCEDURE FOR THE ACQUISITION OF DATA FOR THE DETECTION OF ANGIOGENESIS IN LOWER LIMBS

(71) Applicants: Servicio Andaluz de Salud, Seville (ES); Universidad de Córdoba, Córdoba (ES)

(72) Inventors: José García-revillo García, Seville (ES); Miguel Canis López, Seville (ES); Noelia Romero Mata, Córdoba (ES)

(73) Assignees: Servicio Andaluz de Salud, Seville (ES); Universidad de Córdoba, Córdoba (ES)

( * ) Notice: Subject to any disclaimer, the term of this patent is extended or adjusted under 35 U.S.C. 154(b) by 61 days.

(21) Appl. No.: 15/624,074

(22) PCT Filed: Dec. 14, 2015

(86) PCT No.: PCT/ES2015/070901
§ 371 (c)(1),
(2) Date: Jun. 15, 2017

(87) PCT Pub. No.: WO2016/097443
PCT Pub. Date: Jun. 23, 2016

(65) Prior Publication Data
US 2017/0360382 A1    Dec. 21, 2017

(30) Foreign Application Priority Data

Dec. 15, 2014   (ES) .................................. 201431836

(51) Int. Cl.
*A61B 6/00*    (2006.01)
*A61B 6/03*    (2006.01)

(52) U.S. Cl.
CPC .............. *A61B 6/032* (2013.01); *A61B 6/481* (2013.01); *A61B 6/486* (2013.01); *A61B 6/50* (2013.01); *A61B 6/504* (2013.01); *A61B 6/507* (2013.01); *A61B 6/5217* (2013.01)

(58) Field of Classification Search
CPC ......... A61B 6/032; A61B 6/482; A61B 6/481; A61B 6/486; A61B 6/50; A61B 6/504; A61B 6/507; A61B 6/5217
See application file for complete search history.

(56) References Cited

U.S. PATENT DOCUMENTS

| 8,233,968 B1 * | 7/2012 | Yannacone, Jr. .... A61B 5/4312 250/338.1 |
| 2003/0095696 A1 * | 5/2003 | Reeves ..................... G06T 5/20 382/131 |

(Continued)

OTHER PUBLICATIONS

Purdie et al., "Funcational CT imaging of angiogenesis in rabbit VX2 soft-tissue tumor," 2011, Physics in Medicine & Biology, vol. 46, pp. 3161-3175. (Year: 2011).*

(Continued)

*Primary Examiner* — Kiho Kim
(74) *Attorney, Agent, or Firm* — Mintz Levin Cohn Ferris Glovsky and Popeo, P.C.

(57) ABSTRACT

The invention relates to a method for obtaining useful data about the angiogenesis in a patient's lower limbs, and particularly in the lower limbs of patients with diabetes subjected to treatment.

10 Claims, 4 Drawing Sheets

(56) References Cited

U.S. PATENT DOCUMENTS

2015/0238656 A1* 8/2015 Orlando ............. A61L 27/3633
424/423
2018/0256509 A1* 9/2018 Friedman ............. A61K 9/5146

OTHER PUBLICATIONS

Fraioli et al., "Whole-tumer perfusion CT in patients with advanced lung adenocarcinoma treated with conventional and antiangiogenetic chemotherapy," 2011, Radiology, vol. 259, No. 2, pp. 574-582 (Year: 2011).*
Francesco Fraioli et al, "Whole-Tumor perfusion CT in patients with advanced lung anedocarcinoma treated with conventional and antiangiogenetic chemotherapy: Initial experience", Radiology, vol. 259, No. 2, May 1, 2011.
Guang Chen, "Computed tomography perfusion in evaluating the therapeutic effect of transarterial chemoembolization fo hepatocellular carcinoma", World Journal of Gastroenterology, vol. 14, No. 37, Jan. 1, 2008.
Cao Ning et al, "Monitoring the effects of anti-angiogenesis on the radiation sensitivity of pancreatic cancer xenografts using dynamic contrast-enhanced computed tomography", International Journal of Radiation: Oncology Biology Physics, Pergamon Press, USA, vol. 88, No. 2, Jan. 9, 2014.
Seldinger S.I., "Catheter replacement of the needle in percutaneous arteriography. A new technique.", Acta Radiol. (Stockholm), 39, 368, 1953.
Rafael Ruiz-Salmerón et al, "Angiographic Demonstration of Neoangiogenesis Alter Intra-arterial Infusion of Autologous Bone Marrow Mononuclear Cells in Diabetic Patients UIT Critical Limb Ischemia," Cell Transplantation, vol. 20, p. 1629-1639, Apr. 1, 2011.
Meier P., Zierler KL., "On the theory of the indicator-dilution method for measurement of blood flow and blood volume," J App Physiol Jun. 1954 6(12):731-44.
Axel L., "Cerebral blood flow determination by rapid-sequence computed-tomography: theoretical analysis." Radiology 137: 679-686, Dec. 1980.
Lee TY, Purdie TG, and Stewart E, "CT imaging of angiogenesis"; Q J Nucl Med. Sep. 2003; 47(3):171-87).
International Search Report and Written Opinion issued in corresponding International Application No. PCT/ES2015070901, dated Apr. 4, 2016, 10 pages.
Prezzi, D. et al., "Perfusion CT Imaging of Treatment Response in Oncology," European Journal of Radiology, vol. 84, No. 12, pp. 2380-2385, Mar. 27, 2015.

* cited by examiner

PROCEDURE FOR THE ACQUISITION OF DATA FOR THE DETECTION OF ANGIOGENESIS IN LOWER LIMBS

CROSS-REFERENCE TO RELATED APPLICATIONS

This application is a national stage entry, filed under 35 U.S.C. § 371, of International Application No. PCT/ES2015/070901, filed on Dec. 14, 2015, which claims the benefit of and priority to Spanish Patent Application No. P201431836, filed on Dec. 15, 2014, the entire contents of which are incorporated herein by reference in their entirety.

OBJECT OF THE INVENTION

The present invention belongs to the field of medicine, and more specifically to the field of methods for monitoring angiogenesis in a patient's lower limbs, for example in diabetics.

The object of the present invention is a new method for obtaining useful data about the angiogenesis in a patient's lower limbs.

BACKGROUND OF THE INVENTION

Diabetics are particularly prone to presenting serious ischemic processes that usually affect the more distal vessels (infrapopliteal location), i.e., those vessels belonging to the patient's lower limbs. It is referred to as critical lower limb ischemia. The distal location of lesions in the lower limbs makes the surgical or endovascular revascularization thereof difficult, so in a large proportion of these patients, due to the anatomical extension and distribution of arterial occlusive disease, the ischemia continues its inexorable course until causing amputation of the affected limb.

Standard treatment today for these patients in whom surgical or endovascular revascularization are impossible includes pharmacological treatments. However, it has not yet been proven that pharmacological treatments improve the symptoms of lower limb ischemia. Alternatively, cell therapy and gene therapy have been developed in recent years. The advantage of cellular administration in angiogenesis induction is that it could promote vascular and tissue regeneration directly, as well as the release of different angiogenic growth factors.

In this context, for the purpose of monitoring the patient's progression and making the most suitable medical decisions, it is very important to obtain information relating to whether or not angiogenesis is taking place after administration of the treatment. Angiogenesis can briefly be defined as the physiological process consisting of the formation of new blood vessels from preexisting vessels. In order to determine if angiogenesis is in fact taking place, the "gold standard" technique considered today is arteriography.

Essentially, an arteriography starts by puncturing and catheterizing an artery (usually the common femoral artery) using to that end the Seldinger technique (see "Catheter replacement of the needle in percutaneous arteriography. A new technique." *Acta Radiol.* (Stockholm), 39, 368, 1953). Subsequently, a multiperforated catheter is placed in the infrarenal abdominal aorta on the level of vertebral body L3 and successive X-ray series are taken with iodinated contrast focused on both lower limbs. The contrast material is entrained by the blood flow of the artery and gradually opacifies the network of arteries from a larger to a smaller size until reaching the tissues. Finally, the venous return of the contrast material takes place.

Figure 1A:
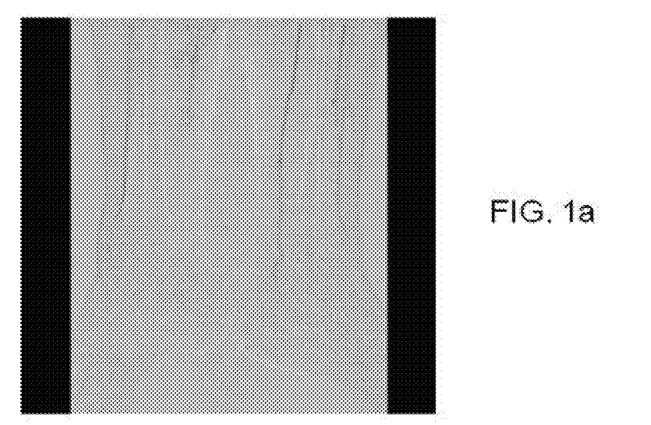
FIGS. 1a-1e show a example of images obtained by means of conventional arteriography of the lower limbs according to the prior art, respectively corresponding to an early or initial arterial phase, an advanced arterial phase, a late arterial phase (precapillary), an early venous phase, and an advanced venous phase.
Figure 1B:
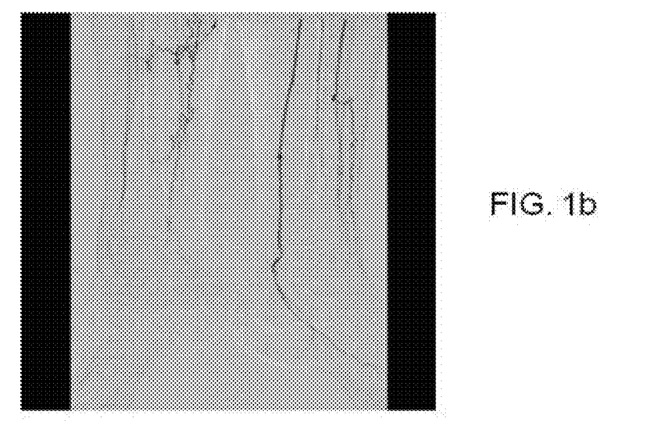
Figure 1C:
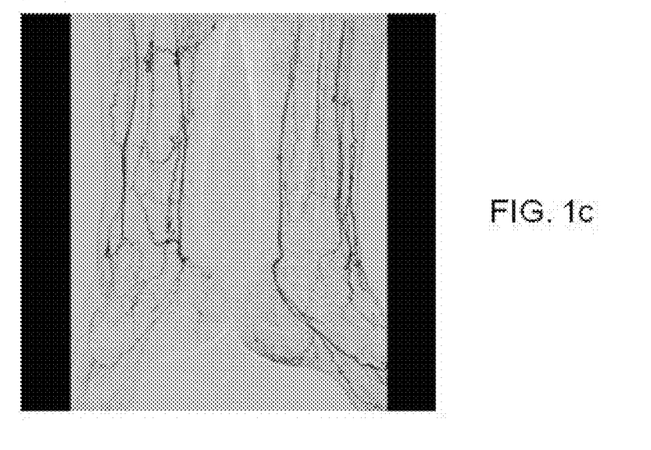
Figure 1D:
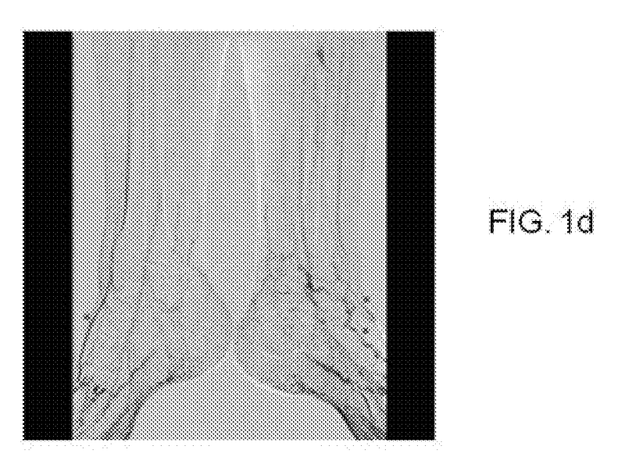
Figure 1E:
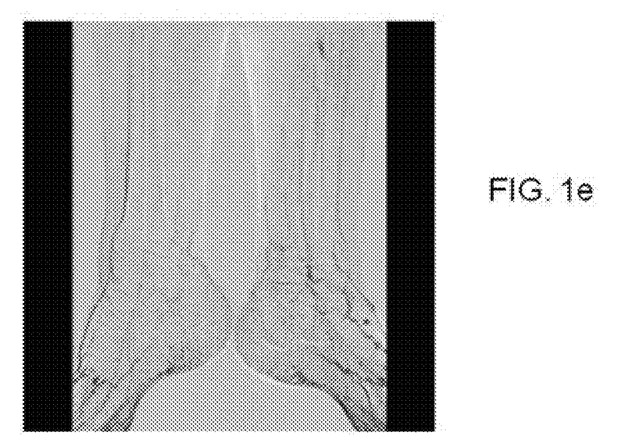

Throughout this entire process, successive flat images of the limbs in question are acquired by means of a digital angiograph. The acquired images have a aspect similar to that shown in FIGS. 1a-1e, where it can be seen how the contrast starts to reach the arteries of the patient's lower limbs (FIGS. 1a and 1b) until reaching a maximum (FIG. 1c), after which the contrast starts to be withdrawn by the venous route (FIGS. 1d and 1 e). These figures allow seeing where the blood flow reaches at a point in time before starting treatment and they allow comparison with equivalent images from the same patient taken after administering treatment. For example, images can be taken before starting treatment and then be repeated 6 or 12 months later. However, this method has various drawbacks, some of which are mentioned below.

Firstly, it is an invasive procedure, meaning that it involves arterial puncturing and catheterization with its subsequent risks. As a result, it furthermore requires hospitalization for at least 24 hours in order to monitor and control the puncture area.

Secondly, it is not easy to get the images obtained before the treatment and the images obtained in subsequent controls to match up entirely, primarily due to the patient's movements at the time of acquiring the images, among other causes. As a result, the position and trajectory of the patient's different arteries do not exactly match up in both images, which often times makes a correct comparison difficult. Today there is software called "Metamorph" ("Angiographic Demonstration of Neoangiogenesis Alter Intraarterial Infusion of Autologous Bone Marrow Mononuclear Cells in Diabetic Patients UIT Critical Limb lschemia," *Cell Transplantation*, Vol. 20, p. 1629-1639, 2011) created specifically for this purpose. However, this software requires the two images to be compared to be identical, and after thorough testing, it has had to be ruled out because this is not possible in most cases.

Thirdly, even though the images obtained using arteriography allow observing the arteries having at least a given minimum size with relative clarity, it is impossible to view the smaller vessels, such as capillaries for example. This is an important drawback for the evaluation of the angiogenesis, because the improvement sometimes occurs precisely as a result of the generation of capillaries, without there being observable changes in larger vessels.

Finally, the comparative study between images taken before and after treatment is performed today in a completely "subjective" manner by visually assessing the presence or absence of new vessels or growth of preexisting vessels (angiogenesis). Furthermore, arteriography does not provide quantifiable data with respect to tissue perfusion.

DESCRIPTION OF THE INVENTION

A number of conventional multislice spiral CT scanners today include a specific software tool called perfusion CT, providing a series of parameters that allow determining the characteristics of the blood flow through the patient's vessels. A number of said parameters, which can generally be referred to as "perfusion parameters," are the following:

| Parameter | Interpretation | Biological meaning |
| --- | --- | --- |
| Blood flow (BF) | Blood flow circulating through the vasculature of the tissue studied per | Oxygen and nutrient |

-continued

| Parameter | Interpretation | Biological meaning |
|---|---|---|
| mL per 100 g/min | unit of time | supply rate |
| Blood volume (BV) mL per 100 g | Blood volume circulating through the vasculature of an area of the studied tissue | Functional blood vessels |
| Mean transit time (MTT) Seconds | Average time it takes the contrast agent to go from the arterial area to the venous area | Perfusion pressure |
| Permeability surface (PS) mL per 100 g/min | Contrast agent flowing from the extracellular plasma to the interstitial space | Vessels with disrupted permeability |

The authors of the present invention have discovered that some of these perfusion parameters currently used in other fields, such as in oncology or for determining the infarcted areas in cases of cerebral infarctions, for example, are useful for identifying areas where angiogenesis takes place in the lower limbs of patients with diabetes subjected to treatment.

Furthermore, the method of the invention is based on taking transverse slices of the patient's lower limbs, unlike conventional arteriography where flat images are used. Using transverse slices allows more precisely identifying the positions of the slices, thereby achieving much higher repeatability. In fact, it can readily be seen that it is much simpler to mark the position and orientation of a plane perpendicular to the patient's lower limb, for example by taking as a reference fixed points throughout the patient's bone structure, than it is to do it in a radiological coronal slice where all of the patient's structures are superimposed along the lower limb.

Additionally, unlike the previous methods where assessment is subjective, the perfusion parameters used in this invention provide objective values representative of the vascular perfusion of the patient's lower limb tissues. This allows making quantitative estimates as to the magnitude of the angiogenesis that is taking place.

Furthermore, by using a CT scanner for obtaining images there are not as many movement artifacts like in digital angiography, which will aid with pre- and post-treatment comparative studies.

Another advantage additional is that the contrast agent is introduced through the venous route instead of the arterial route. It is therefore of a non-invasive method having fewer potential risks than arteriography and does not require hospitalization.

The invention describes a method for obtaining useful data about the angiogenesis in a patient's lower limbs after injecting a contrast agent into the patient. This contrast agent can be an iodinated contrast agent and can be injected by intravenous route instead of by arterial route, as has been the case up until now, thereby constituting an important advantage of this method in relation to the prior art as it prevents the need for patient catheterization and hospitalization. The method fundamentally comprises the following steps:

1) Taking at least one time series of successive transverse slices in at least one position of the patient's limb by means of a CT scanner.

The simplest version of the method of the invention can be carried out by taking a single time series of slices corresponding to a single position. However, as will be described herein in further detail below, a plurality of time series of transverse slices corresponding to several positions along the patient's limb can be taken. In that case, the CT scanner can take a "scout" such that it runs along the positions of the transverse slices several times, acquiring one image in each of said positions for each pass.

In either case, taking the time series of transverse slices preferably starts a number of seconds after injecting the contrast agent in order to give said agent time to reach the patient's lower limb, for example between 13 seconds and 15 seconds after injection.

As regards the position of this time series of slices, it is determined such that it matches up exactly with the position of a corresponding time series of slices taken at an earlier point in time, for example before starting treatment. To that end, any bone reference point of the patient can be used, such as the tibial plateau or the tibial condyles, for example.

In this context, observe that due to the actual configuration of the CT scanner the images or transverse slices that are acquired are not strictly parallel to one another but rather follow spiral pattern. For the sake of simplicity, this will not be taken into account in the present description.

2) Obtaining a perfusion CT image corresponding to said at least one time series of successive transverse slices.

In this step, a perfusion CT image is calculated from the set of images constituting the at least one time series of transverse slices acquired in the preceding step, where each point of the image corresponds to the blood perfusion value at that point. This method is well-known in the art, as will be described herein more specifically below.

The result of this operation is one perfusion CT image for each of the time series of transverse slices taken in the preceding step.

3) Selecting an analysis region in said at least one perfusion CT image.

In this step, the analysis region to be studied is selected. Usually, this region corresponds to all the soft tissues of the patient's lower limb that are shown in the obtained perfusion CT image, excluding bone areas. As will be seen below in reference to the drawings, it is easy to distinguish the soft tissues from the bone areas in the perfusion CT image, since the bone areas have a known shape and position and are shown to be black due to the absence of perfusion. The selection of the analysis region can be done in two ways.

a) Manual selection of the analysis region in the perfusion CT image by the physician or user. In this case, it will only be necessary to mark the complete contour of the patient's lower limb and exclude the contours of the bone areas corresponding to the tibia and fibula.

b) Automatic selection of the analysis region in the perfusion CT image by means of. In this case, it would be enough for the analysis region to include those pixels of the image with a perfusion value greater than a minimum threshold value selected such that only the bone areas are outside the selection.

According to a preferred embodiment of the invention, if the method comprises taking a plurality of time series of slices corresponding to different positions, it is enough to select the analysis region in a perfusion CT image corresponding to a slice position so that this selection is extrapolated to the rest of the perfusion CT images corresponding to the rest of the slice positions.

The analysis region can cover the entire cross section of the patient's lower limb except for bone areas. Alternatively, the analysis region can be split into an anterior portion essentially corresponding to the area of the tibial muscle and a posterior portion essentially corresponding to the area of the calf muscle and the soleus muscle (i.e., the lower leg). Splitting the analysis region into these two portions allows determining in an independent manner if angiogenesis exists in any of them. For example, there may be angiogenesis only in the posterior area of the patient's leg but not in the anterior area. This splitting of the analysis region allows identifying this fact because it allows calculating the parameters and evaluating the presence of angiogenesis in an independent manner for the anterior portion and the posterior portion of the patient's lower limb.

4) Calculating the perfusion parameters BF (Blood Flow) and/or BV (Blood Volume), and PS (Permeability Surface Area Product) corresponding to the analysis region selected in the preceding perfusion CT image.

The parameters PS and BF and/or BV are then calculated (since the values of the parameters BF and BV are normally coupled, only one of them can be calculated) in the selected analysis region in the at least one perfusion CT image described. The mathematical model used for obtaining these parameters is defined in many scientific papers as well as in documents published by CT scanner manufacturers, such as General Electric, Philips or Siemens, for example. The following scientific papers to that effect can be mentioned by way of example:

Meier P., Zierler K I. "On the theory of the indicator-dilution method for measurement of blood flow and blood volume," *J App Physiol* 1954 Jun. 6(12):731-44.

L. Axel. "Cerebral blood flow determination by rapid-sequence computed-tomography: theoretical analysis." *Radiology* 137: 679-686, December 1980.

Lee T Y1, Purdie T G, and Stewart E in "CT imaging of angiogenesis"; *Q J Nucl Med.* 2003 September; 47(3):171-87.

Therefore, it is a method of the state of the art even though up until now it had only been applied to tissues in oncology (antiangiogenic effects) or in neurology to assess ischemic areas.

5) Comparing said calculated perfusion parameters with previously obtained perfusion parameters in order to determine if angiogenesis is taking place.

In this step, a comparison is performed between the calculated perfusion parameters BF (Blood Flow) and/or BV (Blood Volume) and PS (Permeability Surface Area Product) and the parameters obtained at a point prior to starting treatment.

To interpret the results of this comparison, the authors of the present invention conducted a study in 12 patients with critical lower limb ischemia in whom endovascular or surgical revascularization is impossible and who are subjected to intraarterial treatment with stem cells to favor angiogenesis. The parameters BF, BV and PS were monitored and the value of said parameters correlated to the presence or absence of angiogenesis, as well as to other clinical data useful for diagnosis.

The result of the study consists of the criteria shown in the following table for the comparison of the perfusion CT parameters obtained at the initial point and at the point after treatment. As can be seen, these criteria allow determining not only if new blood vessels are being formed in the patient's lower limbs, but it also provides additional information useful for understanding the condition of the patient's vessels.

| BF/BV (generally coupled) | PS | Interpretation |
|---|---|---|
| ↑ | ↑ | Formation of new vessels (angiogenesis) with varying degrees of maturation |
| ↓ | ↓ | Necrosis |
| ↓ | ↔ or ↑ | Inflammation/granulation tissue/early fibrosis |
| ↔ or ↓ | ↑↑ | Poor compartmentalization of the contrast agent Very immature vessels |

In an alternative embodiment of the invention, the method further comprises the step of calculating the perfusion parameter TTM, corresponding to the analysis region selected in the perfusion CT image for use in the determination of the presence of angiogenesis. Calculating the perfusion parameter TTM provides additional information that allows implementing a way of assessing the possible presence of angiogenesis that is an alternative to that described in the preceding table. Specifically, an improvement in at least two of the parameters BF, BV, PS and TTM is preferably interpreted as indicative of the presence of angiogenesis, improvement being defined as an increase of at least 5% for the parameters BF, BV and PS and a decrease of at least 5% for the parameter TTM.

Additionally, the method can comprise the step of calculating the number of blood vessels from the at least one perfusion CT image obtained for comparing it with the number of blood vessels existing at an earlier point in time, for example before treatment. The blood vessels can be counted manually by simply identifying them visually (since they are shown to be red), or they can be counted using image analysis techniques.

In definitive, the method for obtaining useful data about angiogenesis in a patient's lower limbs, briefly, comprises the following steps:

taking at least one time series of successive transverse slices in at least one position of a the patient's limb by means of a CT scanner;

obtaining a perfusion CT image corresponding to said at least one time series of successive transverse slices;

selecting an analysis region in said at least one perfusion CT image;

calculating the perfusion parameters BF and/or BV, and PS corresponding to the analysis region selected in the previous perfusion CT image; and comparing said calculated perfusion parameters with previously obtained perfusion parameters in order to determine whether or not angiogenesis exists.

Although the method of the invention has been described specifically for being carried out by the processing means of a CT scanner, it is understood that it could also be carried out with any other type of processing means to which the CT images of the transverse slices on which the method is based are provided. Therefore, the invention also relates to computer programs suited for any of such processing means to be able to carry out said processes. Such programs can be in the form of source code, object code, an intermediate source code and object code, for example, in a partially compiled form, or in any other form suitable for use in putting the processes according to the invention into practice. The computer programs also cover cloud applications based on said method.

The invention particularly covers computer programs arranged on or in a carrier. The carrier can be any entity or device capable of supporting the program. When the program is incorporated in a signal that can be conveyed directly through a cable or another device or means, the carrier can be made up of said cable or other device or means. As a variant, the carrier could be an integrated circuit in which the program is included, the integrated circuit being suitable for executing, or for being used in the execution of, the corresponding processes.

For example, the programs could be incorporated in storage medium, such as ROM memory, a CD ROM memory or a semiconductor ROM memory, a USB memory, or a magnetic recording medium, for example, a floppy disk or a hard drive. Alternatively, the programs could be supported in a transmissible carrier signal. For example, it could be an electric or optic signal that could be conveyed through electric or optic cable, by radio or by any other means.

PREFERRED EMBODIMENT OF THE INVENTION

An example of the method according to the present invention is described below in reference to the attached drawings. The study conducted to determine the relationship between the parameters BF, BV and PS and the onset or absence of angiogenesis is then described. Finally, several specific examples are described.

Method of the Invention

Positioning

Figure 2:
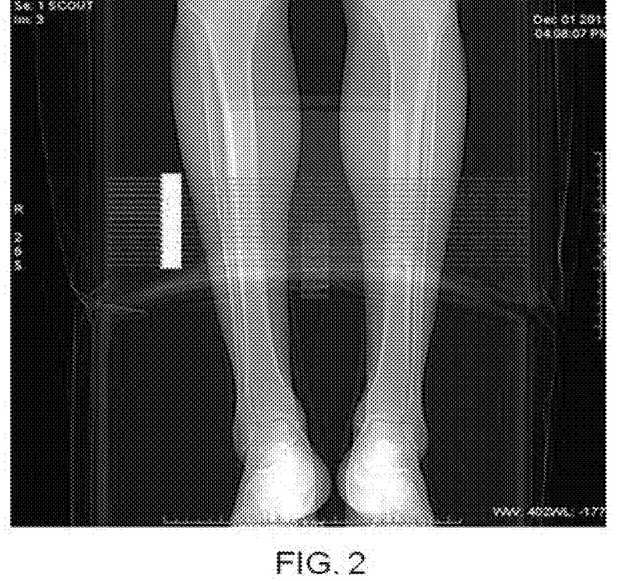
FIG. 2 shows the positions corresponding to 16 respective time series of transverse slices of a patient's lower limbs.

Firstly, a prior procedure aimed at precisely positioning the block of slices of the CT scan is performed to take transverse slices of the patient's lower limbs. To that end, once the patient is introduced in the CT gantry, the block of slices is centered on both legs and a planning scanogram is performed in a coronal plane that includes from the tibial plateau to the foot. In the obtained image, which is shown in FIG. 2, the distance existing between the lower end of the tibia (tibial condyle) and the upper end of the tibia (tibial plateau) is measured, and the block of slices is moved until being located at the midpoint between both. In this specific example the midpoint is taken as a reference because it is an area of the leg where there is a sufficient amount of soft tissue to perform the method of the invention.

Once the position of the midpoint is determined, the block of slices can be located at several parallel positions along the patient's lower limb in order to take a number of series of transverse slices. In this example, 16 time series of transverse slices corresponding to the 16 positions shown in FIG. 2 will be performed.

Injection of the Contrast Agent

The intravenous injection can be performed in an arm of the patient, for example using an automatic injector. The administered contrast agent will spread to the right heart cavities to subsequently return through the pulmonary veins to the left atrium and left ventricle. From here, the distribution of the contrast agent will be an arterial distribution to end up reaching the patient's lower limbs.

More specifically, in this example 0.5 ml of iodinated contrast of 370 mg/mL per kg of the patient's weight are injected by intravenous route. Subsequently, 30 ml of physiological serum are injected. The injection is performed at a rate of 5 ml/s.

Taking CT Images

The start of CT imaging is preferably performed with a delay of between 13 and 15 seconds in relation to the time of the injection of the contrast agent, more preferably 14 seconds. This delay specific has been determined through several tests with different patients to assure that the first CT image that is acquired is immediately prior to the arrival of the contrast agent to the patient's lower limb. Therefore each time series of transverse slices covers the times immediately prior to the arrival of the contrast agent and the tissue perfusion phase of the soft tissues in infrapopliteal region.

As mentioned above, 16 time series of transverse slices corresponding to 16 different positions along the patient's lower limb are taken in this example. According to a preferred embodiment of the invention, each time series can comprise the acquisition of between 20 and 30 CT images for a total approximate time of between 100 seconds and 150 seconds. For example, in this case specific 25 CT images have been acquired during a total approximate time of 120 seconds. In other words, approximately one CT image has been acquired in each position every 5 seconds.

Figure 3:
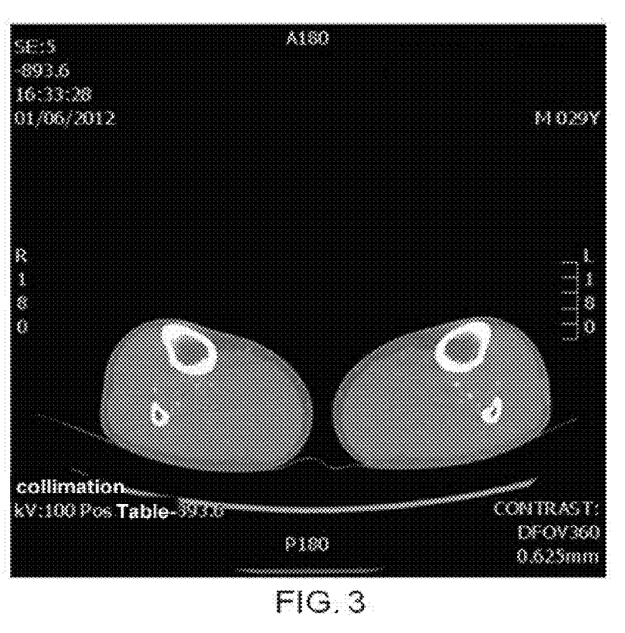
FIG. 3 shows an example of a raw image corresponding to a transverse slice of the lower limbs taken by means of a CT scanner.

The obtained CT images are similar to FIG. 3, in which a cross section of the different internal structures of the patient's lower limb can be seen. The patient's tibia and fibula are seen in a light color, almost white, the patient's soft tissues are seen in grey; and again, the contrast agent going through the patient's blood vessels can be seen in a light color, almost white. Each blood vessel is seen in this image almost as a point, which differs from the branched structure that was obtained while obtaining images of coronal slices according to the prior art. Actually, by taking a complete series of CT images in 120 seconds, the white points corresponding to the vessels would start to appear as the contrast agent reaches them and would fade away after a few seconds.

Obtaining Perfusion CT Images

Based on each of the 16 time series of CT images obtained corresponding to each of the 16 positions, the necessary calculations for determining the blood perfusion value in each point of the image are performed. Starting from that information, an image like the one shown in FIG. 4, corresponding to a slice where the values of the perfusion obtained by the CT scan are represented through a color code, is built for each of the 16 time series.

Figure 4:
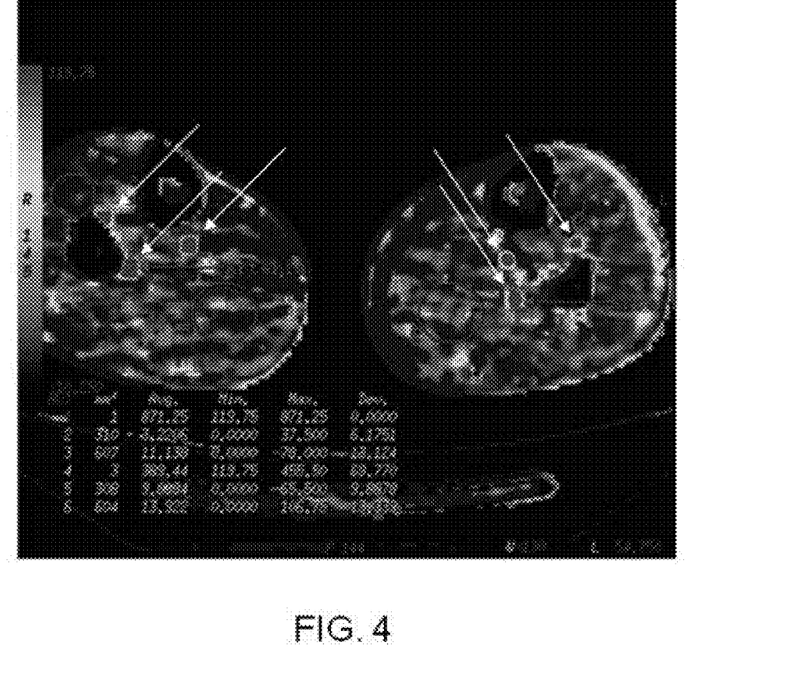
FIG. 4 shows an example of a perfusion CT image corresponding to the preceding transverse slice, where a color code represents the blood perfusion value at each point.

Due to the provisions of Patent Law November 1986 currently in force, FIG. 4 is shown in black and white, although it must be taken into account that in the original image the points where the perfusion is high are seen in red and the points with low perfusion are seen in blue. In this example, arrows indicate the position of the three most visible arteries in each limb, although it must be understood that the color image allows identifying arteries with even further clarity, because they are red colored areas immersed in a blue colored background.

This operation results in obtaining 16 perfusion CT images similar to that of FIG. 4 corresponding to each of the 16 positions of the transverse slices, where each point of each image corresponds to the blood perfusion value in that point.

Calculation of the Parameters

In this example, the parameters BF, BV, MTT and PS defined are calculated. To that end, the user must only select the analysis region in at least one of the 16 perfusion CT images obtained in the preceding step. The analysis region must include all the soft tissue of the patient's limb except the bones. The selection of the analysis region can preferably be done manually by the physician or user. Alternatively, the selection step can be performed automatically by means of a computer program. The selection of said analysis region is extrapolated to each of the 15 remaining images, and then the parameters BF, BV, MTT and PS corresponding to said analysis region are calculated.

Interpretation of the Obtained Values

Finally, once the parameters BF, BV, MTT and PS have been calculated, the obtained values are compared with those that were obtained at another time, for example before starting treatment, which allows determining not only if angiogenesis has taken place, but also additional data helping to interpret what is happening in the tissue.

Study in Patients

The study was conducted in 11 patients in which the parameters BF, BV, MTT and PS were determined according to the described method. This process was carried out a first time before starting treatment (month 0) and a second time three months after treatment (month 3). Patterns in the variation of the parameters were evaluated taking into account the Rutherford-Becker classification.

The result was the following:

| BF/BV (generally coupled) | PS | Interpretation |
| --- | --- | --- |
| ↑ | ↑ | Formation of new vessels (angiogenesis) with varying degrees of maturation |
| ↓ | ↓ | Necrosis |
| ↓ | ↔ or ↑ | Inflammation/granulation tissue/early fibrosis |
| ↔ or ↓ | ↑↑ | Poor compartmentalization of the contrast agent. Very immature vessels |

EXAMPLES

A series of examples corresponding to the patients included in the described study are presented below. The calculated values of BF, BV, MTT and PS in month 0 and in month 3, as well as the conclusion reached according to the present method, are shown for each of them.

Patient 1

|  | BF Soft tissues | BV Soft tissues | MTT Soft tissues | PS Soft tissues |
| --- | --- | --- | --- | --- |
| Month 0 | 351 | 11.7 | 1.99 | 1.89 |
| Month 3 | 360 | 14.9 | 6.54 | 1.88 |
| Conclusion | ↑ | ↑ | ↑ | ↔ |

Since BF/BV increased and PS was maintained, it is concluded that angiogenesis exists.

It is verified that this is consistent with an improvement in the clinical picture, with an increase in the ABI (Ankle-brachial Index) and the TcO2P (Transcutaneous Oxygen Pressure), and with an improvement in the Rutherford-Becker classification.

Patient 2 (Lower Right Limb)

|  | BF Soft tissues | BV Soft tissues | MTT Soft tissues | PS Soft tissues |
| --- | --- | --- | --- | --- |
| Month 0 | 7.52 | 0.816 | 16.4 | 2.10 |
| Month 3 | 9.58 | 1.77 | 18.3 | 3.61 |
| Conclusion | ↑ | ↑ | ↑ | ↑ |

Since the BF/BV increased and PS also increased, it is therefore determined that angiogenesis exists.

It is verified that this is consistent with an improvement in the clinical picture, with an increase in ABI and TcO2P, and with an improvement in the Rutherford-Becker classification.

Patient 2 (Lower Left Limb)

|  | BF Soft tissues | BV Soft tissues | MTT Soft tissues | PS Soft tissues |
| --- | --- | --- | --- | --- |
| Month 0 | 7.03 | 0.800 | 19.2 | 1.35 |
| Month 3 | 9.11 | 1.28 | 20.9 | 2.15 |
| Conclusion | ↑ | ↑ | ↑ | ↑ |

Since the BF/BV increased and PS also increased, it is therefore determined that angiogenesis exists.

It is verified that this is consistent with an improvement in the clinical picture, with an increase in ABI and TcO2P, and with an improvement in the Rutherford-Becker classification.

Patient 3

|  | BF Soft tissues | BV Soft tissues | MTT Soft tissues | PS Soft tissues |
| --- | --- | --- | --- | --- |
| Month 0 | 6.84 | 0.457 | 13.9 | 0.60 |
| Month 3 | 5.09 | 0.378 | 12.7 | 0.791 |
| Conclusion | ↑ | ↔ | ↑ | ↔ |

Since BF/BV decreased or were maintained and PS was maintained, it is therefore determined that angiogenesis does not exist.

This is consistent with the need for subsequent amputation of this patient's limb.

Additional Examples

Additional examples are described below where the analysis region has been split into an anterior portion and an anterior portion, and where to assess the presence of angiogenesis an alternative method with respect to the method described above is used. In the following additional examples it is considered that there is presence of angiogenesis if an improvement of at least two of the parameters BF, BV, PS and TTM is observed, improvement being defined as an increase of at least 5% for parameters BF, BV and PS and a decrease of at least 5% for parameter TTM.

Patient 4

The data corresponding to the posterior and anterior areas of both legs of one and the same patient is shown below:

|  | BF Soft tissues | BV Soft tissues | TTM Soft tissues | PS Soft tissues |
|---|---|---|---|---|
| LOWER RIGHT LIMB | | | | |
| Posterior area (initial) | 33.3 | 2.65 | 14.3 | 3.69 |
| Posterior area (final) | 32.5 | 2.91 | 16.3 | 6.32 |
| Conclusion | ↔ | ↑ | ↑ | ↑ |
| Anterior area (initial) | 12.0 | 3.21 | 23.1 | 4.55 |
| Anterior area (final) | 10.7 | 2.35 | 24.7 | 5.38 |
| Conclusion | ↓ | ↓ | ↑ | ↓ |
| LOWER LEFT LIMB | | | | |
| Posterior area (initial) | 31.7 | 2.27 | 12.1 | 3.55 |
| Posterior area (final) | 62.7 | 6.4 | 13.9 | 16.0 |
| Conclusion | ↑ | ↑ | ↓ | ↑ |
| Anterior area (initial) | 1.91 | 1.69 | 13.6 | 3.22 |
| Anterior area (final) | 11.0 | 1.28 | 16.5 | 3.66 |
| Conclusion | ↑ | ↑ | ↓ | ↑ |

According to this data, it can be seen that in the posterior area of the lower right limb there was an improvement of two parameters, specifically parameters BV and PS. Therefore, it is interpreted that angiogenesis exists in this area. The same happens with both the anterior and posterior areas of the lower left limb, because an improvement in all the parameters can be seen.

Patient 5

| LOWER LEFT LIMB | BF Soft tissues | BV Soft tissues | TTM Soft tissues | PS Soft tissues |
|---|---|---|---|---|
| Posterior area (initial) | 10.5 | 1.44 | 19.6 | 3.81 |
| Posterior area (final) | 34.4 | 4.66 | 15.8 | 10.5 |
| Conclusion | ↑ | ↑ | ↓ | ↑ |
| Anterior area (initial) | 13.1 | 2.08 | 17.3 | 8.55 |
| Anterior area (final) | 39.8 | 4.53 | 15.1 | 14.3 |
| Conclusion | ↑ | ↑ | ↓ | ↑ |

In view of this data, it is concluded that there is improvement in both the anterior and posterior areas of the patient's analyzed lower limb, because all the analyzed parameters have experienced improvement.

The invention claimed is:

1. A method for assessing the presence of angiogenesis in a patient's lower limbs after injecting a contrast agent in the patient, characterized in that it comprises the following steps:
    taking at least one time series of successive transverse slices in at least one position of the patient's limb by means of a CT scanner;
    obtaining a perfusion CT image corresponding to said at least one time series of successive transverse slices;
    selecting an analysis region in said at least one perfusion CT image;
    calculating the perfusion parameters BF, BV, PS, and TTM corresponding to the analysis region selected in the preceding perfusion CT image;
    comparing said calculated perfusion parameters with previously obtained perfusion parameters in order to determine if angiogenesis is taking place, wherein there is presence of angiogenesis if an improvement of at least two of the parameter BF, BV, PS, and TTM is observed, improvement being defined as in increase of at least 5% for parameters BF, BV, and PS and a decrease of at least 5% for parameter TTM; and
    wherein taking the time series of transverse slices starts between 13 seconds and 15 second after injecting the contrast agent.

2. The method according to claim 1, where taking the time series of transverse slices starts 14 seconds after injecting the contrast agent.

3. The method according to claim 1, where taking the time series of transverse slices comprises acquiring between 20 and 30 CT images during a total time of between 100 seconds and 150 seconds.

4. The method according to claim 3, where taking the time series of transverse slices comprises acquiring 25 CT images during a total time of 120 seconds.

5. The method according to claim 1, which comprises taking a plurality of time series of transverse slices corresponding to several positions along the patient's limb.

6. The method according to claim 1, where the selection of the analysis region is done by manually selecting the contour of said analysis region.

7. The method according to claim 1, where the selection of the analysis region is done automatically by selecting only those pixels the perfusion value of which is above a minimum threshold value.

8. The method according to claim 1, where the selection of the analysis region in a perfusion CT image corresponding to a slice position is extrapolated to the rest of the perfusion CT images corresponding to the rest of the slice positions.

9. The method according to claim 1, where the analysis region is split into an anterior portion essentially corresponding to the area of the tibial muscle and a posterior portion essentially corresponding to the area of the calf muscle and the soleus muscle.

10. The method according to claim 1, further comprising the step of calculating the number of blood vessels from the obtained perfusion CT image.

* * * * *